United States Patent [19]

Larkins, Jr. et al.

[11] 4,389,532

[45] Jun. 21, 1983

[54] PROCESS FOR THE PREPARATION OF ACETALDEHYDE

[75] Inventors: Thomas H. Larkins, Jr.; Guy R. Steinmetz, both of Kingsport, Tenn.

[73] Assignee: Eastman Kodak Company, Rochester, N.Y.

[21] Appl. No.: 376,975

[22] Filed: May 10, 1982

[51] Int. Cl.$^3$ .............................................. C07C 47/06
[52] U.S. Cl. ................... 568/487; 568/902; 252/430
[58] Field of Search ............... 568/487, 902; 252/430

[56] References Cited

U.S. PATENT DOCUMENTS

| | | | |
|---|---|---|---|
| 4,111,837 | 9/1978 | Taylor | 252/430 |
| 4,133,966 | 1/1979 | Pretzer et al. | 568/902 |
| 4,151,208 | 4/1979 | Pretzer et al. | 568/487 |
| 4,171,461 | 10/1979 | Bartish | 568/902 |
| 4,239,704 | 12/1980 | Pretzer et al. | 568/487 |
| 4,239,705 | 12/1980 | Pretzer et al. | 568/487 |
| 4,239,924 | 12/1980 | Pretzer et al. | 568/487 |
| 4,239,925 | 12/1980 | Pretzer et al. | 568/487 |
| 4,306,091 | 12/1981 | Gauthier-Lafaye | 568/487 |
| 4,320,230 | 3/1982 | Doyle | 568/487 |
| 4,328,375 | 5/1982 | Barlow | 568/487 |
| 4,348,541 | 9/1982 | Doyle | 568/487 |

OTHER PUBLICATIONS

Wender et al., "Science", vol. 113 (1951), pp. 206–207.
Mizoroki et al., "Bull. Chem. Soc.", Japan, vol. 37 #2 (1964), pp. 236–241.

*Primary Examiner*—Werren B. Lone
*Attorney, Agent, or Firm*—David E. Cotey; Daniel B. Reece, III

[57] ABSTRACT

The present invention provides a process for the preparation of acetaldehyde from hydrogen, carbon monoxide, and methanol. The process comprises conducting the reaction in the presence of a catalyst system comprising cobalt, platinum, and iodide. The cobalt catalyst component is present in a concentration of about 0.01 to 1 weight percent, the platinum catalyst component is present in a concentration of about 0.03 to 3 weight percent, and the iodide catalyst component is present in a concentration of about 0.1 to 40 weight percent, as defined herein. The weight ratio of cobalt to platinum is about 1:0.3 to 1:35. The process is preferably conducted at a temperature of 160°–230° C. and a pressure of 10,000–70,000 kPa.

16 Claims, No Drawings

PROCESS FOR THE PREPARATION OF ACETALDEHYDE

BACKGROUND OF THE INVENTION

The present invention relates to the preparation of acetaldehyde from hydrogen, carbon monoxide, and methanol under carbonylation conditions. The reaction is conducted in the presence of a catalyst system comprising cobalt, platinum, and iodide.

It is known that cobalt catalyzes the formation of acetaldehyde from methanol, carbon monoxide, and hydrogen. For example, it was disclosed by Wender et al., *Science*, 113, 206-7 (1951), that a cobalt carbonyl catalyst system could be used. However, the product of the disclosed process was primarily ethanol, together with a small amount of acetaldehyde. It was later shown that the addition of iodide to a cobalt-containing catalyst system increased the amount of acetaldehyde which was produced, although ethanol was still the major product (see, for example, T. Mizoroki et al., *Bull. Chem. Soc. Japan*, 37, 2, 236-41 (1964)). U.S. Pat. No. 4,239,925 also discloses a cobalt-iodide catalyst system in which small quantities of acetaldehyde were produced along with the desired ethanol product. It has additionally been disclosed that trivalent phosphorous, nitrogen, arsenic, or antimony compounds may be used to further increase the production of acetaldehyde in the presence of cobalt-iodide catalyst systems (see, for example, U.S. Pat. Nos. 4,151,208 and 4,239,704).

Various transition metals, especially the metals of Group VIII, have been employed in cobalt-iodide catalyst systems. However, the objective and the result has been to achieve improvements in the production of ethanol. For example, U.S. Pat. Nos. 4,133,966 and 4,239,924 disclose the addition of ruthenium to a cobalt-iodide catalyst system. It has been reported that the addition of sodium iodide to a cobalt-ruthenium-methyl iodide catalyst system retards the hydrogenation of acetaldehyde to ethanol (see T. Mizoroki et al., *Bull. Chem. Soc. Japan*, 52, 2, 479-82 (1979)). However, the primary product continues to be ethanol. U.S. Pat. No. 4,111,837 discloses that the addition of rhenium to a cobalt-iodide catalyst system also improves ethanol production. The rate of formation of ethanol was also improved by the addition of rhodium and boron to a cobalt-iodide catalyst system (U.S. Pat. No. 4,171,461).

Each of the prior art references mentioned above reports acetaldehyde production at low to moderate chemical yields and production rates. Large amounts of by-products, such as acetic acid, ethyl acetate, methyl acetate, etc., were produced. Also, in each of the references, ethanol was the primary product.

U.S. Pat. No. 3,856,856 discloses that carboxylic acids and esters thereof can be produced by contacting alcohols with carbon monoxide at elevated temperature and pressure in the presence of a catalyst system comprising cobalt, iodide ion, and a platinum promoter. The product mixture obtained by the described process comprises almost totally acetic acid and methyl acetate, with acetaldehyde being present, if at all, in only minute quantities.

Thus, there existed a need for a catalyst system which would provide improved selectivity for acetaldehyde at increased production rates. It has now been found that a cobalt-platinum-iodide catalyst system provides the desired selectivity for acetaldehyde in the reaction of methanol with carbon monoxide and hydrogen (synthesis gas).

SUMMARY OF THE INVENTION

The present invention provides a process for the preparation of acetaldehyde from hydrogen, carbon monoxide, and methanol. The process comprises conducting the reaction at carbonylation temperature and pressure in the presence of a catalyst system comprising cobalt, platinum, and iodide.

DETAILED DESCRIPTION OF THE INVENTION

The present invention resides in a process for the preparation of acetaldehyde from hydrogen, carbon monoxide, and methanol which comprises conducting the reaction in the presence of a catalyst system comprising cobalt, platinum, and iodide.

The cobalt component of the catalyst system can be provided in a variety of forms. Preferably, the cobalt component is derived from a soluble source of cobalt, such as the salt of a lower alkanoic acid having 2-10 carbon atoms, e.g., acetic, propionic, butyric, etc. A specific example of such a salt is cobalt acetate tetrahydrate, which is especially preferred as a source of cobalt for the catalyst system of the present invention. Also useful are cobalt halides, such as cobalt fluoride, cobalt chloride, cobalt bromide, and cobalt iodide, and other cobalt salts such as nitrates, sulfates, carbonates, etc. Cobalt carbonyl complexes, such as $Co_2(CO)_8$, are also suitable.

The cobalt catalyst component is present in the catalyst system in a concentration of about 0.01 to 1 weight percent. The cobalt catalyst component is preferably present in a concentration of about 0.02 to 0.1 weight percent. The term "weight percent" as used herein refers to the number of grams of cobalt metal which is present in the reaction system per 100 grams of methanol.

The platinum catalyst component can be derived from any suitable platinum source. Such sources include platinum metal and inorganic or organic compounds of platinum. Suitable platinum compounds include chloroplatinic acid, platinic acid, platinum tetrachloride, ammonium hexachloroplatinate, platinic oxide, platinous oxide, platinum dichloride, platinum diiodide, platinum cyanide, platinum hydroxide, etc. Especially preferred as a platinum source is $PtCl_2$.

The platinum catalyst component is present in the reaction system in a concentration of about 0.03 to 3 weight percent (e.g., about 0.05 to 0.3 weight percent). The term "weight percent" as here used denotes the number of grams of platinum metal present in the reaction system per 100 grams of methanol.

The cobalt and platinum catalyst components are preferably provided in amounts such that the weight ratio of cobalt metal to platinum metal is about 1:0.3 to 1:35. In especially preferred embodiments, the weight ratio of cobalt to platinum is about 1:2 to 1:7.

The iodide ion component of the catalyst system of the present invention may be provided in the form of free iodine or in the form of an iodine compound. Illustrative iodine compounds include hydrogen iodide (generally in the form of an aqueous solution), alkali metal iodides, and the alkyl iodides derived from lower alcohols containing up to four carbon atoms, e.g., methyl iodide. Especially preferred iodine compounds include lithium iodide, methyl iodide, and hydrogen iodide, with lithium iodide being especially preferred. Of course, the cobalt component and the iodide component may be provided as a combination, for example, in the form of cobalt iodide.

The iodide catalyst component is present in a concentration of about 0.1 to 40 weight percent. Preferably, the iodide component is present in a concentration of about 1 to 10 weight percent. The term "weight percent" as here used refers to the number of grams of iodide present in the reaction system per 100 grams of methanol.

The catalyst system of the present invention may include additional promoters. Typical promoters include organic phosphines, arsines, and stibines. Specific examples of such promoters include triphenyl phosphine, triphenyl arsine, triphenyl stibine, etc. Such promoters may be included in the catalyst system without particular detriment to the process.

The present process uses as starting materials methanol, carbon monoxide, and hydrogen. The methanol reactant may be provided in the form of derivative products which revert to the alcohol under conditions of the process. Such derivatives include ethers, alkyl halides, and esters. For example, the feedstock may comprise methanol, dimethyl ether, methyl acetate, or combinations thereof.

The carbon monoxide and hydrogen reactants are preferably provided as a mixture, e.g., in the form of synthesis gas. Synthesis gas can be prepared from a wide range of hydrocarbon raw materials including natural gas, petroleum and petroleum residues, coal, etc., by well known methods such as steam reforming, partial oxidation, coal gasification, etc.

The relative amounts of hydrogen and carbon monoxide present in the reaction mixture can be varied over a wide range. However, the molar ratio of hydrogen to carbon monoxide typically is in the range of about 10:1 to 1:10. The molar ratio of hydrogen to carbon monoxide is preferably about 3:1 to 1:3. However, conventional synthesis gas having a molar ratio of about 1:1 is convenient and satisfactory for the process of the present invention.

The present process can be conducted under conditions of temperature and pressure which are typical for carbonylation reactions. For example, the reaction is preferably conducted at a temperature of 160°–230° C. (e.g., 180°–200° C.). The pressure which is employed in the process of the present invention preferably is in the range of 10,000–70,000 kPa and is most preferably about 20,000–30,000 kPa.

While applicants do not wish to be bound by theoretical considerations, it appears that the advantageous results of the present process are due to a stabilizing effect which the platinum catalyst component has upon the cobalt-iodide catalyst system. It has been observed that other transition metals, such as rhodium, ruthenium, iridium, etc., do not demonstrate this stabilizing quality. The enhancement of the efficacy of a cobalt-iodide catalyst system in the production of acetaldehyde by the presence of platinum in the catalyst system has not hitherto been disclosed in the art.

This invention will be further illustrated by the following examples although it will be understood that these examples are included merely for purposes of illustration and are not intended to limit the scope of the invention.

EXAMPLES 1–4

In each of Examples 1–4, 3.5 moles of methanol (4.0 moles of methanol in Example 4) and the indicated quantities of platinum dichloride, cobalt acetate, and lithium iodide were loaded into a 300 ml Hastelloy C autoclave designed to operate in a rocking mode. In Examples 1–3, the $PtCl_2$ concentration was 0.20 grams (0.13 weight percent platinum metal), the cobalt acetate concentration was 0.20 g (0.06 weight percent cobalt metal), and the lithium iodide concentration was varied from 1.0 to 9.0 grams (0.85 to 7.62 weight percent iodide). In Example 4, the cobalt acetate concentration was 0.50 grams (about 0.13 weight percent cobalt metal), the platinum chloride concentration was about 0.25 grams (about 0.14 weight percent platinum metal), and the iodide concentration was 9.0 g (about 6.7 weight percent iodide).

The autoclave was purged with about 700 kPa of a gas mixture comprising hydrogen and carbon monoxide in a 1:1 molar ratio at room temperature. The gas was then vented from the autoclave. The autoclave internal pressure was then increased to about 70 kPa by adding the $CO/H_2$ gas mixture at room temperature. The autoclave was sealed, heated, and rocked until the reaction temperature of 195° C. was attained, at which time additional $CO/H_2$ gas mixture was added in order to increase the autoclave internal pressure to about 27,000 kPa. The time at which the autoclave internal pressure reached the predetermined value was taken as the time at which reaction was initiated. Reactor pressure was maintained at the predetermined value during the course of the reaction by adding the $CO/H_2$ gas mixture at the same rate at which it was consumed by the reactants. When the predetermined reaction time of 30 minutes was completed, the autoclave was rapidly cooled by a stream of cold air. After the gas was vented from the autoclave, the reaction product was analyzed by gas chromatographic methods using a Poropak Q column with an acetonitrile internal standard. In some runs, a small amount of the dimethyl acetal of acetaldehyde was formed. Concentrated sulfuric acid was added to all samples prior to injection into the gas chromatograph to decompose any acetal into methanol and acetaldehyde. All reported values for acetaldehyde in the following Examples reflect this acid treatment. The products obtained in each of Examples 1–4 are listed in Table I.

TABLE I

| Ex. | Catalyst Component (g) | | | Products (moles) | | | | | | | | | Space Time Yield (g AcH/l hr) | Conversion (%) |
|---|---|---|---|---|---|---|---|---|---|---|---|---|---|---|
| | $PtCl_2$ | $Co(OAc)_2$ | LiI | MeOH | $H_2O$ | AcH | MeI | MeOAc | HOAc | EtOH | EtOAc | Crot | | |
| 1 | 0.20 | 0.20 | 1.0 | 3.02 | 0.67 | 0.51 | 0.001 | 0.032 | — | — | 0.001 | — | 321 | 14.3 |
| 2 | 0.20 | 0.20 | 5.0 | 2.46 | 1.07 | 0.90 | 0.007 | 0.078 | — | — | 0.007 | 0.003 | 566 | 29.7 |
| 3 | 0.20 | 0.20 | 9.0 | 2.11 | 1.12 | 0.96 | 0.009 | 0.106 | — | — | 0.010 | 0.004 | 604 | 39.7 |
| 4 | 0.25 | 0.50 | 9.0 | 2.50 | 1.30 | 0.92 | 0.003 | 0.13 | — | 0.007 | 0.012 | — | 507 | 37.5 |

It can be seen from a review of the data of Table I that the present process provides excellent selectivity for acetaldehyde, with acetaldehyde being the major organic product recovered and with ethanol being detected in trace amounts, if at all.

It can further be seen that the addition of increasing amounts of the iodide catalyst component improves the space-time yield and the conversion, but produces additional amounts of by-products. Thus, the optimal concentration of iodide in a particular system will depend upon the desired rate and selectivity for that system.

COMPARATIVE EXAMPLES 1-4

These Comparative Examples illustrate the effect of the iodide catalyst component and the platinum catalyst component upon the inventive process.

These Comparative Examples were conducted in the same manner and under the same conditions as previously described, using the indicated amounts of the catalyst components. Comparative Example 4 utilized 4.0 moles of methanol. The results of Comparative Examples 1-4 are given in Table II.

EXAMPLES 5-10

These Examples illustrate the effect of temperature on the process of the present invention.

The present examples were conducted in the same manner and under the same conditions as previously described except that the temperature was varied from 160°-230° C., as indicated in Table III. The catalyst system for all of the present examples comprised 0.20 grams $PtCl_2$, 0.20 grams cobalt acetate, and 9.0 grams lithium iodide. The results are given in Table III.

TABLE III

| Example | Temp. (°C.) | MeOH | $H_2O$ | AcH | MeI | MeOAc | HOAc | EtOH | EtOAc | Crot | $CH_4$ |
|---|---|---|---|---|---|---|---|---|---|---|---|
| 5 | 160 | 3.00 | 0.73 | 0.45 | 0.016 | 0.106 | — | — | 0.001 | — | 0.016 |
| 6 | 180 | 2.47 | 0.89 | 0.57 | 0.022 | 0.12 | — | — | 0.003 | 0.002 | — |
| 7 | 195 | 2.15 | 1.20 | 0.81 | 0.016 | 0.13 | 0.002 | — | 0.005 | 0.004 | 0.058 |
| 8 | 205 | 2.37 | 0.95 | 0.58 | 0.011 | 0.081 | — | — | 0.004 | 0.002 | 0.076 |
| 9 | 215 | 1.97 | 1.32 | 0.78 | 0.013 | 0.097 | 0.013 | — | 0.009 | 0.006 | 0.16 |
| 10 | 230 | 1.74 | 1.40 | 0.65 | — | 0.105 | 0.025 | 0.012 | 0.019 | 0.010 | 0.37 |

It can be seen from a review of the data of Table III that the process of the present invention is operative within the entire range of 160°-230° C. It can further be seen that the selectivity for acetaldehyde is excellent over the entire range of temperatures, with best results being achieved in the middle of the temperature range, around 195° C. Temperatures above 195° C. result in the formation of increasing amounts of methane.

The invention has been described in detail with particular reference to preferred embodiments thereof, but it will be understood that variations and modifications can be effected within the spirit and scope of the invention.

TABLE II

| Comp. Ex. | Catalyst Component (g) | | | Products (moles) | | | | | | | | | Space Time Yield (g AcH/l hr) | Conversion (%) |
|---|---|---|---|---|---|---|---|---|---|---|---|---|---|---|
| | $PtCl_2$ | $Co(OAc)_2$ | LiI | MeOH | $H_2O$ | AcH | MeI | MeOAc | HOAc | EtOH | EtOAc | Crot | | |
| 1 | 0.20 | 0.20 | — | 3.88 | 0.09 | 0.03 | 0.001 | 0.004 | — | — | — | — | — | — |
| 2 | — | 0.20 | 1.0 | 3.08 | 0.46 | 0.36 | — | 0.026 | — | — | — | — | 226 | 12.0 |
| 3 | — | 0.20 | 9.0 | 2.84 | 0.44 | 0.28 | 0.017 | 0.051 | — | — | — | — | 176 | 18.9 |
| 4 | — | 0.50 | 9.0 | 3.36 | 0.59 | 0.35 | 0.026 | 0.085 | — | — | — | — | 192 | 16.0 |

It can be seen from a review of the data of Table II that the iodide component is necessary to the effectiveness of the catalyst system of the present invention. For example, a comparison of the results of Comparative Example 1 (in which the catalyst system did not include an iodide component) with the results of Examples 1-3 (which utilized 1.0 to 9.0 g of LiI) reveals that very little reaction occurs in the absence of iodide.

A comparison of the results of Comparative Examples 2-4 (in which the catalyst system did not include a platinum component) with the results of Examples 2-4 (which utilized 0.20 to 0.25 g of $PtCl_2$) reveals the advantages due to the addition of platinum to the catalyst system. For instance, the results of Example 1 represent a marked improvement over those of Comparative Example 2. Likewise, the results of Example 3 were better than those of Comparative Example 3, and the results of Example 4 were better than those of Comparative Example 4. Thus, the use of a catalyst system comprising platinum, cobalt, and iodide provides improved selectivity and rate of reaction for the production of acetaldehyde.

We claim:

1. A process for the preparation of acetaldehyde from hydrogen, carbon monoxide, and methanol which comprises conducting the reaction at carbonylation temperature and pressure in the presence of a catalyst system comprising cobalt, platinum, and iodide.

2. The process of claim 1 wherein said reaction is conducted at a temperature of 160° to 230° C.

3. The process of claim 1 wherein said reaction is conducted at a pressure of 10,000 to 70,000 kPa.

4. The process of claim 1 wherein the cobalt catalyst component is present in a concentration of about 0.01 to 1 weight percent.

5. The process of claim 1 wherein the platinum catalyst component is present in a concentration of about 0.03 to 3 weight percent.

6. The process of claim 1 wherein the concentration of the iodide catalyst component is about 0.1 to 40 weight percent.

7. The process of claim 1 wherein the weight ratio of cobalt to platinum is about 1:0.3 to 1:35.

8. A process for the preparation of acetaldehyde from hydrogen, carbon monoxide, and methanol which comprises conducting the reaction at a temperature of 160° to 230° C. and a pressure of 10,000 to 70,000 kPa in the presence of a catalyst system comprising cobalt, platinum, and iodide, the cobalt catalyst component concentration being about 0.01 to 1 weight percent, the platinum catalyst component concentration being about 0.03 to 3 weight percent, and the iodide catalyst component concentration being about 0.1 to 40 weight percent, with the weight ratio of cobalt to platinum being about 1:0.3 to 1:35.

9. The process of claim 8 wherein said reaction is conducted at a temperature of 180° to 200° C.

10. The process of claim 8 wherein said reaction is conducted at a pressure of 20,000 to 30,000 kPa.

11. The process of claim 8 wherein the cobalt catalyst component is present in a concentration of about 0.02 to 0.1 weight percent.

12. The process of claim 8 wherein the platinum catalyst component is present in a concentration of about 0.05 to 0.3 weight percent.

13. The process of claim 8 wherein the iodide catalyst component is present in a concentration of about 1 to 10 weight percent.

14. The process of claim 8 wherein the weight ratio of cobalt to platinum is about 1:2 to 1:7.

15. A process for the preparation of acetaldehyde from hydrogen, carbon monoxide, and methanol which comprises conducting the reaction at a temperature of 180° to 200° C. and a pressure of 20,000 to 30,000 kPa in the presence of a catalyst system comprising cobalt, platinum, and iodide, the cobalt catalyst component concentration being about 0.02 to 0.1 weight percent, the platinum catalyst component concentration being about 0.05 to 0.3 weight percent, and the iodide catalyst component concentration being about 1 to 10 weight percent, with the weight ratio of cobalt to platinum being about 1:2 to 1:7.

16. In a process for the preparation of acetaldehyde for hydrogen, carbon monoxide, and methanol which comprises conducting the reaction at carbonylation temperature and pressure, the improvement comprising conducting said reaction in the presence of a catalyst system comprising cobalt, platinum, and iodide.

* * * * *